United States Patent [19]

Van Berkel et al.

[11] 4,258,205
[45] Mar. 24, 1981

[54] 2,2-DIMETHYLCYCLOPROPANECAR-BALDEHYDE DIMETHYL ACETAL DERIVATIVES

[75] Inventors: Johannes Van Berkel; Hendrik C. Kelderman, both of Amsterdam, Netherlands

[73] Assignee: Shell Oil Company, Houston, Tex.

[21] Appl. No.: 965,951

[22] Filed: Dec. 4, 1978

[30] Foreign Application Priority Data

Dec. 16, 1977 [GB] United Kingdom ............... 52463/77
Dec. 16, 1977 [GB] United Kingdom ............... 52464/77
Dec. 16, 1977 [GB] United Kingdom ............... 52465/77

[51] Int. Cl.³ .................. C07C 43/315; C07C 47/37; C07C 69/14
[52] U.S. Cl. .................................. 560/231; 560/238; 560/240; 562/506; 568/303; 568/342; 568/420; 568/591
[58] Field of Search ............... 560/231; 568/591, 420; 260/598

[56] References Cited

U.S. PATENT DOCUMENTS 3,527,769  9/1970  Matsui et al. .................. 560/231
3,708,528  1/1973  Mukherjee et al. .................. 560/231
3,723,469  3/1973  Martel .............................. 260/343.3

OTHER PUBLICATIONS

Houben-Weyl, Methoden der Org. Chemie, vol. VII, Part 1, 159-192, (1954), vol. VIII, 418-423 and 638-639, (1952).
Chem. Reviews, 58, pp. 925-995, (1958).
J. Org. Chem., 35, No. 11, 4000-4002, (1970).

*Primary Examiner*—Vivian Garner

[57] ABSTRACT

New 2,2-dimethylcyclopropanecarbaldehyde dimethyl acetal derivatives of the formula

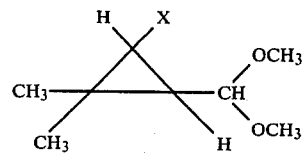

wherein X is —CH$_2$OC(O)CH$_3$, —CH$_2$OH, or —CHO are useful chemical intermediates for the preparation of pesticidally active cyclopropanecarboxylates.

4 Claims, No Drawings

2,2-DIMETHYLCYCLOPROPANECARBALDE-HYDE DIMETHYL ACETAL DERIVATIVES

BACKGROUND OF THE INVENTION

1. Field of the Invention

This invention relates to new 2,2-dimethylcyclopropanecarbaldehyde dimethyl acetal derivatives and to a process for the preparation of these derivatives.

2. Description of the Prior Art

It is well known that certain substituted cyclopropanecarboxylic acid derivatives are an important class of pesticides called "pyrethroids". These pyrethroids have been of considerable interest because of their quick knock-down activity, low persistence as toxic residues and their low mammalian toxicity. However, the acid moiety of these pyrethroids has heretofore been fairly expensive to manufacture in the large scale commercial quantities for agricultural and domestic applications.

The hereinafter described process of the invention, and the new intermediates thereof, provide a method for obtaining desired pyrethroids from 3-carene, which is an inexpensive, readily available, naturally occurring terpene found in numerous varieties of pine trees.

SUMMARY OF THE INVENTION

The present invention is directed to new 2,2-dimethylcyclopropanecarbaldehyde dimethyl acetal derivatives of formula I

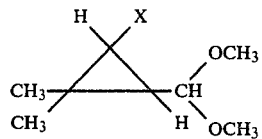

wherein X is —CH$_2$OC(O)CH$_3$, —CH$_2$OH or —CHO, useful as intermediates for the preparation of certain pesticidally active cyclopropanecarboxylates of the "pyrethroid" type, and to a process for the preparation of the acetal derivatives of formula I.

One specific embodiment of the invention is 3-acetoxymethyl-2,2-dimethylcyclopropanecarbaldehyde dimethyl acetal of formula II

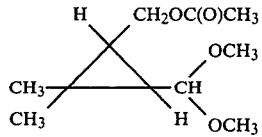

This compound is prepared by ozonolysis of the corresponding 2-(3-acetoxymethyl-2,2-dimethylcyclopropyl)vinyl acetate of formula X

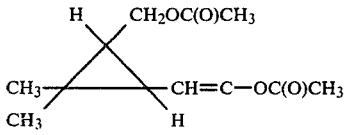

followed by reduction of the ozonolysis product formed in the presence of a lower alkanol, such as methanol, ethanol or the like, and in the presence of an acetalizing catalyst such as p-toluenesulphonic acid. The reduction is suitably carried out using dimethyl sulphide.

Ozonolysis of organic compounds and reduction of the peroxidic ozonolysis products formed is described in, for example, Chemical Reviews 58 (1958) 925–995.

The acetal of formula II above is converted into 3-(hydroxymethyl)-2,2-dimethylcyclopropanecarbaldehyde dimethyl acetal of formula III

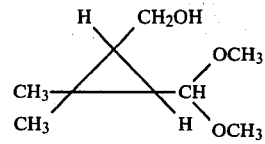

by hydrolysis under conditions in which the two methoxy groups remain unchanged. Hydrolysis of esters is described in, for example, "Methoden der Organischen Chemie" (Houben-Weyl), Volume VIII (1952) 418–423 and 638–639. In the present case, this hydrolysis can be achieved by using an alkaline-reacting medium.

The compound of formula III is a new chemical and a useful intermediate. Oxidation of the compound of formula III under conditions suitable for the conversion of a primary alcohol to an aldehyde produces 3-formyl-2,2-dimethylcyclopropanecarbaldehyde dimethyl acetal of formula IV

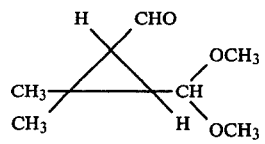

which is also a new chemical and useful intermediate. The oxidation of primary alcohols to aldehydes is described in, for example, "Methoden der Organischen Chemie" (Houben-Weyl), Volume VII, Part 1 (1954) 159–192. The oxidation is suitably carried out with the chromium trioxide-pyridine complex, as described in J. Org. Chem. 35 (1970) No. 11, 4000–4002.

The above described compound of formula IV is a useful chemical intermediate and is converted into a compound of formula V

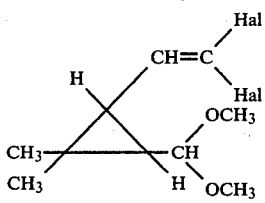

wherein each Hal is independently selected from chlorine, bromine or fluorine, by a two step process described in British patent application 52466/77, filed Dec. 16, 1977, in Great Britain and its corresponding U.S. application Ser. No. 966,681 of Pieter A. Verbrugge, Petrus A. Kramer, Johannes Van Berkel and Hendrik C. Kelderman, filed concurrently with the present application. This process comprises treating a tri(dialkylamino)phosphine or an alkyl ester of an ortho-phosphorous acid bis(dialkylamide) with a compound generating a dihalocarbene :C(Hal)$_2$ in which Hal has the same meaning as defined above and, after the reaction has proceeded virtually to completion, treating the resulting product with a compound of formula IV.

Hydrolysis of the compound of formula V followed by oxidation of the resulting aldehyde product yields 2-(2,2-dihalovinyl)-3,3-dimethylcyclopropanecarboxylic acids, which are used to prepare pyrethroid esters of the type described in U.S. Pat. No. 4,024,163 using procedures disclosed therein.

As stated earlier, the new compounds of the invention are part of a new pyrethroid synthesis route starting from 3-carene. Accordingly, the intermediate X is prepared by a multi-step process in which 3-carene, having the formula VI

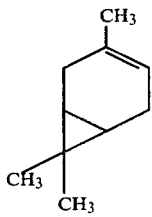

is ozonized to form 1-(2,2-dimethoxyethyl)-2,2-dimethyl-3-(2-oxopropyl)cyclopropane of formula VII

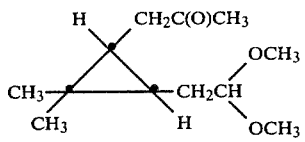

which is oxidized with a strong oxidizing agent, such as m-chloroperbenzoic acid, to (2-(2,2-dimethoxyethyl)-3,3-dimethylcyclopropyl)methyl acetate of formula VIII

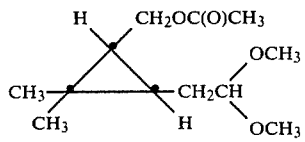

which is hydrolyzed in the presence of acid to (2,2dimethyl-3-(2-formylethyl)cyclopropyl)methyl acetate of formula IX

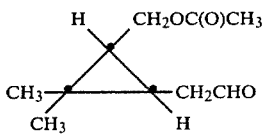

and this compound is treated with acetic anhydride in the presence of a base to yield the compound of formula X.

The compounds of formulas II thru X, inclusive, may have a cis or trans structure or may be a mixture of such isomers, a pure optical isomer or a mixture of optical isomers. When (+)-3-carene is the starting material, the products have predominately the cis-form.

The above described compounds VII, VIII, IX and X, and their preparation, are described and claimed in the concurrently filed U.S. patent application, Ser. No. 953,987 of Steven A. Roman.

ILLUSTRATIVE EMBODIMENTS

The following embodiments serve to further illustrate the invention. Yields and purities were determined by means of gas-liquid chromatography and nuclear magnetic resonance (NMR) spectroscopy. The NMR data quoted were recorded at 90 MHz using solutions of the compounds in deuterochloroform.

EMBODIMENT 1

1-(2,2-dimethoxyethyl)-2,2-dimethyl-3-(2-oxopropyl)- cyclo propane (the compound of formula VII)

A flask was charged with (+)-3-carene (375 mmol) and water-free methanol (150 ml) and kept at a temperature of −60° C. Then, a mixture of ozone and oxygen was passed through the liquid in the flask at a rate of 70 l/h (corresponding to 75 mmol of ozone per hour) until the (+)-3-carene was fully converted (5 hours). The reaction mixture was allowed to react a temperature of 20° C., dimethyl sulphide (750 mmol) and p-toluene sulphonic acid (1.74 mmol) were added and the resulting mixture was stirred for four days at 20° C. At the end of this period, the (+)-3-carene was fully converted into the desired product. Methanol and dimethyl sulphide were evaporated from the reaction mixture at a pressure of 24 mbar (40° C.), diethyl ether (150 ml) was added to the residue obtained, the solution formed was washed with 5%w aqueous sodium hydrogen carbonate (30 ml) and with four 30 ml portions of water, the washed solution was dried over anhydrous magnesium sulphate, and the solvent was evaporated from the dried liquid at a temperature of 30° C. and a pressure of 24 mbar to give a liquid residue (68.9 g). This residue was distilled at 83° C./1 mbar to give a fraction consisting of the cis isomer of the desired product, yield 73.5%.

EMBODIMENT 2

(2-(2,2-Dimethoxyethyl)-3,3-dimethylcyclopropyl)- methyl acetate (the compound of formula VII)

The contents of a flask charged with the product as prepared in Embodiment 1 above (200 mmol), chloroform (300 ml) and m-chloroperbenzoic acid (384 mmol) were stirred at 20° C. for 24 hours. The mixture was separated by filtration, the precipitate was washed with n-pentane (150 ml), the combined filtrates were washed with two 50 ml portions of water, the washed liquid was dried over anhydrous magnesium sulphate, and the solvent was evaporated from the dried liquid at a temperature of 90° C. and a pressure of 20 mbar to give a residue containing the desired product in a yield of 97%. The content of the desired product in the residue was 92%; only the cis isomer had been formed.

EMBODIMENT 3

(2,2-Dimethyl-3-(2-formylethyl)cyclopropyl)methyl acetate (the compound of formula IX)

The contents of a flask charged with the product in the residue prepared in Embodiment 2 above (218 mmol), acetic acid (40 ml) and water (20 ml) were stirred at 60° C. during 2.5 hours. The solvent was evaporated from the reaction mixture at a temperature of 45° C. and a pressure of 24 mbar, the residue obtained was taken up in diethyl ether (150 ml), the solution obtained was washed with two 50 ml portions of a 5%w solution of sodium hydrogen carbonate in water and with two 50 ml portions of water, the washed solution was dried over anhydrous magnesium sulphate, and the solvent was evaporated from the dried liquid at a temperature of 30° C. and a pressure of 24 mbar to give a residue containing the desired product in a yield of 80%; the content of the desired product in the residue was 85%. Only the cis isomer had been formed.

EMBODIMENT 4

2-(3-Acetoxymethyl-2,2-dimethylcyclopropyl)vinyl acetate (the compound of formula X)

The contents of a flask charged with the product in the residue prepared in Embodiment 3 above (175 mmol), triethylamine (386 mmol) and acetic anhydride (350 ml) were stirred at 20° C. for 18 hours. The solvent was evaporated from the reaction mixture at a temperature of 70° C. and a pressure of 20 mbar, the residue obtained was taken up in diethyl ether (150 ml), the solution obtained was washed with five 40 ml portions of water, the solution was dried over anhydrous magnesium sulphate, and the solvent was evaporated from the dried liquid at a temperature of 40° C. and a pressure of 20 mbar to give a residue containing the desired product in a quantitative yield. The content of the desired product in the residue was 88.4%; 64% of the desired product had the cis structure, 36% the trans structure on the carbon-carbon double bond. The orientation to the cyclopropane ring was still cis.

EMBODIMENT 5

3-Acetoxymethyl-2,2-dimethylcyclopropanecarbaldehyde dimethyl acetal (the compound of formula II)

A flask was charged with the product in the residue prepared in Embodiment 4 above (175 mmol), water-free methanol (200 ml) and p-toluenesulphonic acid (1.16 mmol) and kept at a temperature of −65° C. Then, a mixture of ozone and oxygen was passed through the liquid in the flask at a rate of 60 l/h (corresponding to 75 mmol of ozone per hour) until the starting material was fully converted (2.5 hours). The reaction mixture formed was allowed to reach a temperature of 20° C., dimethyl sulphide (350 mmol) was added, and the mixture formed was stirred for 17 hours at 20° C. Methanol and dimethyl sulphide were evaporated from the reaction mixture at a pressure of 16 mbar, diethyl ether (50 ml) was added to the residue obtained and sufficient saturated aqueous solution of sodium bicarbonate was added to the mixture so that the pH reached a value of 7. Then, the mixture was washed with three 50 ml portions of water, the washed liquid was dried over anhydrous magnesium sulphate, and the solvent was evaporated from the dried liquid at a temperature of 40° C. and a pressure of 24 mbar to give a residue (29.6 g) containing the desired product (yield between 51 and 78%). Only the cis isomer had been formed. The NMR spectrum of the desired product showed the following absorptions:

| | |
|---|---|
| $\delta$ = 3.38 ppm (singlet, C—O—C$\underline{H}_3$) | $\delta$ = 1.18 ppm (singlet, H$_3$C—C—C$\underline{H}_3$) |
| $\delta$ = 4.2 ppm (multiplet, $\underline{H}$—C—O—CH$_3$) | $\delta$ = 1.1 ppm (multiplet, H—C—CH$_2$) |
| $\delta$ = 1.2 ppm (multiplet, $\underline{H}$—C—C(H)—(OCH$_3$)$_2$) | $\delta$ = 4.2 ppm (multiplet, H—C—C$\underline{H}_2$) |
| $\delta$ = 1.18 ppm (singlet, $\underline{H}_3$C—C—CH$_3$) | $\delta$ = 2.1 ppm (singlet, $\underline{H}_3$C—C(O)—O—) |

EMBODIMENT 6

3-Hydroxymethyl-2,2-dimethylcyclopropanecarbaldehyde dimethyl acetal (the compound of formula III)

A flask was charged with all of the residue obtained in Embodiment 5 above, water (75 ml), sodium hydroxide (150 mmol) and acetone (25 ml) and the liquid obtained was kept under reflux (60° C.) for three hours. Then, the acetone and part of the water were evaporated at a pressure of 16 mbar, the residue obtained was extracted with five 50 ml portions of diethyl ether (during the last two extractions sufficient sodium chloride was added so that the aqueous phase was saturated with this salt), the combined extracts were dried over anhydrous magnesium sulphate and the solvent was evaporated from the dried liquid at a temperature of 40° C. and a pressure of 24 mbar to give a residue containing the desired product in a yield of 51%, calculated on the product from Embodiment 5. The content of the desired product in the residue was 80%. The cis content of the desired product was 70%. The NMR spectrum of the cis isomer of the desired product showed the following absorptions:

| | |
|---|---|
| $\delta$ = 3.32 ppm (singlet, C—O—C$\underline{H}_3$) | $\delta$ = 1.05 ppm (singlet, $\underline{H}_3$C—C—CH$_3$) |
| $\delta$ = 4.83 ppm (singlet, $\underline{H}$—C—O—CH$_3$) | $\delta$ = 1.2 ppm (multiplet, $\underline{H}$—C—CH$_2$) |
| $\delta$ = 1.53 ppm (doublet, $\underline{H}$—C—C(H)—(OCH$_3$)$_2$) | $\delta$ = 3.8 ppm (doublet, $\underline{H}_2$C—OH) |
| $\delta$ = 1.05 ppm (singlet, $\underline{H}_3$C—C—CH$_3$) | $\delta$ = 4.3 ppm (singlet, H$_2$C—O$\underline{H}$) |

EMBODIMENT 7

3-Formyl-2,2-dimethylcyclopropanecarbaldehyde dimethyl acetal (the compound of formula IV)

A flask was charged with a mixture of pyridine (120 mmol) and methylene chloride (150 ml) and then with chromium trioxide (60 mmol) at a temperature of 20° C. The contents of the flask were stirred for 15 minutes. Then, a solution of 1.74 g of the residue obtained in Embodiment 6 above which contained 6.39 mmol of the desired product of Embodiment 6—in methylene chloride (5 ml) was added to the contents of the flask and stirring was continued for 20 minutes. The precipitate in the flask was allowed to settle, the liquid in the flask was decanted, the precipitate was washed with three 25 ml portions of diethyl ether, the three washings were filtered over a bed of 2 cm Florisil (trademark), the combined three filtrates were washed with two 20 ml portions of a 5%w aqueous solution of sodium hydroxide and then with two 20 ml portions of water and the combined washed ethereal liquids were added to the decanted liquid. The liquid thus obtained was dried over anhydrous magnesium sulphate and the solvent was evaporated from the dried liquid at a pressure of 16 mbar to give a residue containing the desired product in a yield of 59%, calculated on starting material (product from Embodiment 6). The content of the desired product in the residue was 46.5%. The cis content of the desired product was 70%. The NMR spectrum of the cis isomer of the desired product showed the following absorptions:

δ = 3.30 ppm (singlet, C—O—C<u>H</u>₃)
δ = 4.8 ppm (doublet, <u>H</u>—C—O—CH₃)
δ = 1.2 ppm (multiplet, <u>H</u>—C—C(H)—(OCH₃)₂)
δ = 1.22 ppm (singlet, H₃<u>C</u>—C—CH₃)
δ = 1.37 ppm (singlet, <u>H</u>₃C—C—CH₃)
δ = 1.8 ppm (doublet, <u>H</u>—C—C(O)H)
δ = 9.6 ppm (doublet, <u>H</u>—C=O)

We claim:
1. A compound of the formula

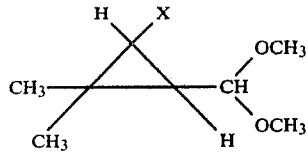

wherein X is —CH₂OH, —CHO or —CH₂OC(O)CH₃ in the cis isomer form.

2. A compound according to claim 1 wherein X is —CH₂OH.

3. A compound according to claim 1 wherein X is —CHO.

4. A compound according to claim 1 wherein X is —CH₂OC(O)CH₃.

* * * * *